United States Patent
Fröhlich et al.

(10) Patent No.: US 9,668,681 B2
(45) Date of Patent: Jun. 6, 2017

(54) MEASURING DEVICE FOR MEASURING CEREBRAL PARAMETERS

(75) Inventors: Jürg Hans Fröhlich, Zürich (CH); Markus Hugo Muser, Wädenswil (CH)

(73) Assignee: NeMoDevices AG, Zurich (CH)

( * ) Notice: Subject to any disclaimer, the term of this patent is extended or adjusted under 35 U.S.C. 154(b) by 91 days.

(21) Appl. No.: 14/115,456

(22) PCT Filed: Feb. 17, 2012

(86) PCT No.: PCT/EP2012/052778
§ 371 (c)(1),
(2), (4) Date: Feb. 6, 2014

(87) PCT Pub. No.: WO2012/150054
PCT Pub. Date: Nov. 8, 2012

(65) Prior Publication Data
US 2015/0011853 A1    Jan. 8, 2015

(30) Foreign Application Priority Data
May 5, 2011 (CH) .......................... 774/11

(51) Int. Cl.
*A61B 5/00* (2006.01)
*A61B 5/1455* (2006.01)
*A61B 5/1459* (2006.01)

(52) U.S. Cl.
CPC ........ *A61B 5/14553* (2013.01); *A61B 5/0084* (2013.01); *A61B 5/1459* (2013.01); *A61B 5/14552* (2013.01)

(58) Field of Classification Search
CPC ................................................. A61B 1/00096
See application file for complete search history.

(56) References Cited

U.S. PATENT DOCUMENTS

| | | | |
|---|---|---|---|
| 4,730,622 A | 3/1988 | Cohen | |
| 4,986,671 A | 1/1991 | Sun et al. | |

(Continued)

FOREIGN PATENT DOCUMENTS

| | | |
|---|---|---|
| EP | 0481612 A1 | 4/1992 |
| EP | 0933061 B1 | 10/2004 |

(Continued)

OTHER PUBLICATIONS

International Searching Authority, International Search Report for International Application No. PCT/EP2012/052778, mailed May 11, 2012, 9 pages, European Patent Office, The Netherlands.

(Continued)

*Primary Examiner* — Tse Chen
*Assistant Examiner* — Joanne Hoffman
(74) *Attorney, Agent, or Firm* — Alston & Bird LLP (57) ABSTRACT

The invention relates to a measuring device and to a method for measuring parameters of a body tissue using an elongate probe (1) for insertion into the body tissue, comprising at least one optical waveguide (2) for transmitting light beams that runs along the longitudinal axis of the probe within the probe, an exit region (5) from which light beams emitted from the optical waveguide exit into the body tissue, and at least one receiving region (6) through which light beams reflected and/or scattered in the body tissue enter the probe as input light beams on a photodetector or in an optical waveguide (2; 3). The exit region (5) is provided at the distal end of the probe (1) and is oriented at least partially in the longitudinal direction of the probe (1). At least some of the emitted light beams exit the probe in the longitudinal direction of the probe. The at least one receiving region (6) is located at a distance from the distal end of the probe on a lateral circumferential region of the probe. The input light beams entering a receiving region (6) are subject to a (Continued)

deflection of more than 90° relative to the light beams emitted from the exit region (5).

16 Claims, 1 Drawing Sheet

(56) References Cited

U.S. PATENT DOCUMENTS

| | | | |
|---|---|---|---|
| 5,090,410 | A | 2/1992 | Saper et al. |
| 5,579,774 | A | 12/1996 | Miller et al. |
| 5,706,821 | A | 1/1998 | Matcher et al. |
| 6,029,671 | A * | 2/2000 | Stevens et al. ............... 128/898 |
| 6,195,574 | B1 | 2/2001 | Kumar et al. |
| 6,261,226 | B1 * | 7/2001 | McKenna et al. ............ 600/109 |
| 6,315,712 | B1 | 11/2001 | Rovegno |
| 6,373,567 | B1 * | 4/2002 | Wise et al. .................... 356/301 |
| 6,447,527 | B1 * | 9/2002 | Thompson et al. .......... 606/174 |
| 6,608,684 | B1 * | 8/2003 | Gelikonov et al. ........... 356/479 |
| 6,697,666 | B1 * | 2/2004 | Richards-Kortum A61B 5/0071 600/478 |
| 7,047,054 | B2 | 5/2006 | Benni |
| 2001/0002250 | A1 * | 5/2001 | Burbank et al. ............... 424/9.5 |
| 2001/0038063 | A1 * | 11/2001 | Mitsuoka et al. ......... 250/201.3 |
| 2003/0071988 | A1 * | 4/2003 | Smith et al. ................... 356/128 |
| 2004/0019293 | A1 * | 1/2004 | Schweitzer, Jr. .. A61B 5/14552 600/549 |
| 2005/0043596 | A1 | 2/2005 | Chance |
| 2005/0165303 | A1 * | 7/2005 | Kleen ................. A61B 5/0071 600/424 |
| 2007/0019916 | A1 | 1/2007 | Takami |
| 2007/0167867 | A1 | 7/2007 | Wolf |
| 2008/0143822 | A1 * | 6/2008 | Wang et al. .................... 348/36 |
| 2012/0136240 | A1 | 5/2012 | Pranevicius et al. |

FOREIGN PATENT DOCUMENTS

| | | |
|---|---|---|
| EP | 1301119 B1 | 6/2005 |
| EP | 2294973 A2 | 3/2011 |
| JP | 2002-010986 A | 1/2002 |
| WO | WO 94/27494 A1 | 12/1994 |
| WO | WO 99/37204 A1 | 7/1999 |
| WO | WO 01/40776 A1 | 6/2001 |
| WO | WO 2005/082225 A1 | 9/2005 |
| WO | WO 2007/064984 A2 | 6/2007 |
| WO | WO 2009/062189 A1 | 5/2009 |
| WO | WO 2010/015094 A2 | 2/2010 |

OTHER PUBLICATIONS

Di Ieva, Antonio, et al., "Analysis of Intracranial Pressure Past, Past, Present, and Future", *The Neuroscientist*, Feb. 6, 2013, pp. 592-603, vol. 19, Issue 6, SAGE Publications Inc, U.S.A.

Fan, J.Y., et al., "Intracranial Pressure Waveform Morphology and Intracranial Adaptive Capacity", *American Journal of Critical Care*, Nov. 2008; pp. 545-554, vol. 17, No. 6., The American Association of Critical-Care Nurses, U.S.A.

Raksin, Patricia B., et al., "Noninvasive Intracranial Compliance and Pressure Based on Dynamic Magnetic Resonance Imaging of Blood Flow and Cerebrospinal Fluid Flow", *Neurosurg Focus*, 2003, 13 pages, vol. 14, No. 4, retrieved from <http://www.medscape.com/viewarticle/452769_print> on Oct. 30, 2015.

Themelis, George, et al. "Near-Infrared Spectroscopy Measurement of the Pulsatile Component of Cerebral Blood Flow and Volume from Arterial Oscillations", *Journal of Biomedical Optics*, Jan. 2007, pp. 014033-1 to 014033-7, vol. 12, Issue 1, International Society for Optics and Photonics, U.S.A.

* cited by examiner

MEASURING DEVICE FOR MEASURING CEREBRAL PARAMETERS

CROSS REFERENCE TO RELATED APPLICATIONS

This application is a national stage application, filed under 35 U.S.C. §371, of International Application No. PCT/EP2012/052778, filed Feb. 17, 2012, which claims priority to Swiss Application No. 0774/11, filed May 5, 2011, the contents of both of which are hereby incorporated by reference in their entirety.

BACKGROUND

Related Field

The invention relates to a measuring device and a method for measuring parameters of a body tissue using an elongated probe for insertion into the body tissue as set forth in the preamble of claim 1, in particular a measuring device for measuring cerebral parameters by means of an invasive measuring procedure.

Description of Related Art

Various invasive procedures for cerebral diagnostics and therapy are known in which different cerebral parameters are measured, such as cerebral hemodynamics. Measured are, for example, parameters relating to the concentration of deoxygenated and oxygenated hemoglobin, the mean transit time of an indicator, the cerebral blood volume, the cerebral blood flow or the tissue oxygen index. Among the methods of this kind are e.g. the near-infrared spectroscopy (NIRS) or the pulse oximetry. For capturing cerebral parameters subdural measurements, measurement on the brain surface, ventricular measurements or intraparenchymal measurements may be carried out.

Known from EP 1301119 B1 is e.g. a subdural probe and a device for measuring cerebral hemodynamics and oxygen saturation. For this purpose the probe comprises a first optical guide, which guides light to the distal end of the probe and thus to the head and into the brain of a patient, and a second optical guide, which guides light from the distal end to a proximally situated processing device. The optical guides are disposed substantially parallel to one another. Provided at the distal end of the optical guides are optical units which deflect light guided by the optical guides out of the transmission direction along the guide by an angle of e.g. 90°. The light is thereby redirected e.g. by the optical units from a direction parallel to the dura vertically into the brain tissue. The optical guides and the optical units form emitting and receiving optodes, and are surrounded by a covering of elongated shape. The spacing of the optical units determines the implantation depth, to which light is able to penetrate into the tissue and be reflected or scattered back. Light reflected or scattered by the brain tissue is directed to the second optical unit, and is thereby fed to the optical guide from a direction approaching perpendicular to the transmission direction, and is guided in transmission direction to the processing device. With such a probe the light exits laterally in radial direction, and reflected and scattered light is also captured again in radial direction on the same side. A significant portion of the light can thereby reach the receiving optode directly on the side of the probe along the surface thereof without penetrating the tissue to be measured. The measurement signal can thereby be interfered with or distorted. Furthermore localization of the measured tissue region is difficult in the case of a measurement on the side of the probe.

Known from U.S. Pat. No. 5,579,774 is moreover a device for measuring the blood flow in cerebral areas, which device can be inserted at a right angle into cerebral tissue. The device has a plurality of sensors along an elongated measuring probe for carrying out a Laser Doppler Flowmetry (LDF) measurement. The sensors are provided at openings along the length and the circumference of the measuring probe and at its tip. The sensors are connected to a light source by means of optical guides which have at the end a reflecting surface that directs the light in a way substantially perpendicular to the measuring probe into the surrounding tissue. The spacing of the sensors must be large to such an extent that light which is emitted from a sensor and is reflected or scattered by the tissue is not able to be captured by another sensor. With this measuring device the emitted and the captured light are thus emitted and captured at the same opening in the measuring probe. The measurable area within the cerebral tissue is thereby limited in an extreme way, and the measurement can be distorted by the emitting and receiving opening being situated together.

U.S. Pat. No. 4,986,671 shows an optical measuring probe for measuring pressure, temperature and flow rate in blood vessels. The measuring probe can be provided on a catheter, which is inserted into the blood vessels. The measuring probe has an optical transmission medium which guides light of different wavelengths to the tip of the probe for measuring different parameters. Provided at the tip of the probe is an elastic optical element which forms an inwardly convex surface that is coated with different materials. Light which is guided by the optical transmission medium to the elastic surface of the optical element is reflected there. The parameters to be measured can be determined from the light that is deflected on the deformed elastic surface, the deformation being characteristic for the parameter values to be measured. With this measuring method no light exits from the measuring probe into the surrounding tissue, so that the measuring range of the probe in the surrounding region is very small. Furthermore some relevant parameters, such as oxygen content, cannot be determined with such a measuring probe.

BRIEF SUMMARY

It is an object of the present invention to create a measuring device and a method for invasive measurement of parameters of a body tissue facilitating a reliable and as precise as possible measurement of different parameters of a body tissue, simplifying a localization of the measured region, only minimally impacting the surrounding tissue and having a simple construction.

These and other objects are achieved through a measuring device for measuring parameters of a body tissue and a method for measuring these parameters according to the independent claims 1 and 13. Special embodiments and/or variants emerge from the subordinate claims.

A measuring device for measuring parameters of a body tissue according to the present invention has an elongated probe for insertion into the body tissue. The probe can have e.g. a cylindrical or also a flattened shape. The probe has a stiff section at the distal end, such as for example a stiff cover or a stiff housing, with which it can be inserted into the body tissue. Such a section is already to be understood as stiff when there is sufficient stability to be able to insert the probe into the body tissue. As a rule, such a section is stiffer than an adjacent element of the probe, such as a catheter tube or the like, for instance, but can however have a certain flexibility or yieldingness in order to make possible a gentle insertion. The stiff section can be provided at one end of a flexible line, such as a catheter tube, for instance. At least one optical or electrical line is provided for transmission of light rays, which line runs substantially along the longitudinal axis of the probe inside the probe, and is guided to the probe through the flexible line. The probe comprises an exit region, out of which exit light rays emitted from the optical guide exit out of the probe into the body tissue, after which the light rays are reflected, scattered and/or absorbed on the body tissue. The probe further comprises a receiving region through which input light rays reflected and/or scattered in the body tissue enter the probe e.g. on a photo detector and/or in an optical guide. For the case of the optical guide, separate optical guides are provided inside the probe for an emitted light ray and a reflected or respectively scattered input light ray. It is not excluded, however, that one optical guide is able to transmit a light ray that exits the probe for measuring the parameters and also a light ray that has been reflected or scattered in the body tissue. The at least one optical guide, or in the case of the photo detector at least one electrical transmission medium can transmit the input light rays as measurement signal to a processing device which determines the parameters to be measured using the input light rays. This can take place e.g. in a known way through analysis of the light intensity or the wavelengths of the input rays in comparison with the emitted light rays. The processing device can be used also for directing the emitted light rays.

According to the present invention, the exit region is provided on the distal end of the probe, and is oriented at least partially in longitudinal direction of the probe. It is thus oriented in beam direction of the light rays guided in the optical guide. The exit region can be situated on a front side of the probe. The exit region can be designed to be approximately symmetrical around the longitudinal axis, and can form the distal termination of the probe. Preferably the surface normal of the exit region coincides with the longitudinal axis of the probe. The light rays emitted out of the exit region exit in distal direction at least partially in longitudinal direction of the probe out of this probe. Preferably the direction of the ray exit out of the exit region lies on the longitudinal axis of the probe. Hence the direction of propagation of the emitted light rays has at least one vector portion which is directed parallel to the longitudinal axis of the probe, respectively of the emitting optical guide, in the direction of the body tissue lying in front of the probe. The emitted light rays can form a bundle of light rays which exit out of the exit region, for example in a straight line along the longitudinal axis, or are also emitted in a cone-shaped way symmetrically around the longitudinal axis, e.g. at an angle to the longitudinal axis.

The at least one receiving region is provided on a lateral circumferential region of the probe in a way spaced apart from the distal end of the probe and thus also spaced apart from the exit region. Thus the receiving region is formed substantially in radial direction to the longitudinal axis. The receiving region can be provided e.g. by means of an aperture or a transparent window in the jacket of the probe. The receiving region serves the purpose of capturing light scattered or reflected on the body tissue. For this purpose the input rays strike a photo detector, for instance, which is provided at the receiving region and is connected to an electrical conductor, or are fed to an optical guide by means of an optical element that is disposed in the probe. A multiplicity of receiving regions can be provided in a distributed way encircling the probe or in longitudinal direction of the probe. An own electrical or optical guide can be provided for each receiving region, or a joint optical guide is used. Received with the receiving region can be preferably both input light rays that run substantially radially to the probe axis, i.e. perpendicular to the receiving region, and also run approximately parallel to the probe axis as well as all input rays running at an angle between these directions.

According to the method for measuring parameters of a body tissue using an above-described measuring device, emitted light rays exit the probe or respectively exit out of the light guide at least partially in longitudinal direction at the distal end of the probe out of the probe, and enter again at a lateral circumferential region of the probe in a way spaced from this exit region, these input light rays entering at a receiving region being subjected to a deflection of more than 90° relative to light rays emitted out of the exit region. Since the direction of propagation of the emitted light rays has at least one small vector portion which is directed from the probe distally forward, i.e. away from at least one receiving region, they must be deflected by more than 90° in order to reach a receiving region and be received as measuring signal. The majority of the emitted light rays are emitted as a rule along the longitudinal axis of the probe, so that predominantly a deflection by more than 190° is necessary so that the input light rays are able to strike the receiving region. It is thus ensured that the emitted light rays undergo a deflection through reflection or scattering at the body tissue before they arrive at the receiving region as input light rays. Excluded can be an exit out of the probe and immediate entrance into the probe without an interaction with the body tissue taking place, as can happen with conventional measuring probes, for example, the receiving area and the exit area being identical or the emitted light rays running along the probe approximately within a guide channel for the probe without entering the body tissue. The light rays are not able to take any bypass course.

As a rule the majority of the emitted rays exit out of the probe at least approximately along the longitudinal axis of the probe, or respectively of the optical guide, and enter the probe again at the receiving region preferably approximately radially to the longitudinal axis of the probe. Thus most of the emitted light rays undergo a deflection in a range of about 270° until entering at a receiving region.

Thus with a measuring device according to the present invention the exit region and the entrance region can lie close to one another and the probe can be constructed shorter without the measuring signal being disadvantageously influenced thereby. The body tissue is thereby less stressed during insertion of the measuring device. Through a symmetrical arrangement of the exit region and the entrance regions around the longitudinal axis of the probe the region of the tissue that will be measured can be determined in a simple way through localization of the position of the probe. It is not necessary to capture an alignment of the probe at a particular position. With the method according to the invention, parameters can be captured relating to blood flow, hemoglobin values, water stored in the brain tissue or diverse markers.

Provided the alignment of the probe is known and individual electrical or optical guides for various receiving regions are used, the evaluation of the parameters can take place for certain subregions around the probe which are assigned to a receiving region. The evaluation of the parameters can thereby be refined.

In one embodiment of the measuring device a spacing of between 1 and 40 mm, preferably between 3 and 20 mm, is provided between an exit region and a receiving region.

Preferably a multiplicity of receiving regions are provided in a way distributed around the circumference of the probe with the same spacing to the exit region. Provided can be, for instance, two diametrically opposed receiving regions or three, four or more preferably symmetrically disposed receiving regions distributed around the circumference. The firm section of the probe, e.g. in the form of a stiff cover or a firm housing, has in one embodiment maximally a length of 50 mm. It preferably has a length of about 20 mm and very preferably 12 mm.

In a variant, the exit region can be provided e.g. as exit aperture or exit window in the probe housing or in a probe cover, through which the light rays emitted out of the light guide exit out of the probe.

In another variant of the measuring device, the exit region can comprise an optical element which terminates the distal end of the probe. The optical element can have a convex or conically outwardly directed surface, the radial diameters tapering in distal direction. Light rays emitted out of the optical guide thus run through the optical element before they exit out of the probe. The optical element itself can form the exit region. The optical element can consist of the same material as the cover around the probe or as the probe housing. For example, the optical element can be made of epoxy resin or a material having comparable optical features such as e.g. polycarbonate, glass, acrylate, polypropylene, polyimide. It is advantageous if the optical element is made of a material with a higher refraction index than the adjacent tissue or the adjacent material. Thus emerging from the optical guide are exiting light rays which run through the optical element on the surface of the optical element in such a way that they are diffracted away from the longitudinal axis of the probe. Also conceivable in principle is the use of a grating which is put into a material that is disposed over the optical guide. Preferably the emitted light ray is widened into a cone of light on the optical element at the distal end of the probe, which cone of light covers a larger region of the body tissue than a light ray exiting directly out of the optical guide. The optical element thus diverts the light rays emitted out of the optical guide in the direction of the at least one receiving region in such a way that a vector portion of the direction of propagation remains in distal direction. The optical element is preferably designed symmetrical around the longitudinal axis of the probe, and forms the distal termination of the probe, which penetrates into the body tissue. The furthermost situated distal region of the optical element is preferably of blunt or respectively curved design, e.g. spherical or elliptical. The optical element can be made of solid material. It can seal off the exit opening of the emitting optical guide. In principle the optical element can have a coating on its surface, for example, which makes easier the insertion of the probe into the body tissue or which supports the diffraction of the light rays.

Furthermore, at the distal end of the probe, the measuring device can have a reflection surface with an aperture through which the optical guide emerges. The emitted light rays are then guided through the aperture and are emitted in distal direction behind the reflection surface. The reflection surface can close off e.g. a cavity of the probe which receives the at least one optical guide. One end of the optical guide emitting the light rays can protrude a little bit through the reflection surface or terminate in a way flush therewith. The reflection surface is preferably aligned perpendicular to the longitudinal axis of the probe, or respectively to the radiation direction of the optical guide. The reflection surface serves the purpose of reflecting back in the direction of the body tissue light rays that are reflected or scattered in the direction of the exit region.

The optical element on the distal end of the probe can be directly adjacent to the reflection surface. It is also possible to dispose the reflection surface on the optical element itself. The optical element can be disposed behind the reflection surface in distal direction. The exit of the emitted light rays out of the optical guide thus lies at or behind the reflection surface and in front of the surface of the optical element. Thus light rays that are possibly reflected on the surface of the optical element can be reflected back to the surface from the reflection surface, so that these light rays do not become lost for the examination of the body tissue.

Light rays with different wavelengths can be used for measuring the parameters in the body tissue. Preferably used is light in the infrared range with one or more wavelengths in the range of between 600 nm and 1000 nm. Light rays with different predetermined wavelengths can also be used that are sent into the body tissue at staggered intervals and in a pulsed way.

In principle further sensors can also be provided on the probe, such as, for example, sensors for temperature or pressure measurement.

A measuring device and a method according to the present invention are particularly suitable for measuring cerebral tissue in that the probe is inserted into the tissue approximately perpendicular to the cranium surface. Since the emission of the light rays takes place at least partially in distal direction, i.e. in direction of insertion of the probe into the tissue, the probe needs to be put less far into the tissue than in the case of a radial emission, in order to be able to measure the same tissue region. Damage to the tissue from the insertion of the probe is thereby minimized.

BRIEF DESCRIPTION OF FIGURES

Preferred embodiments of the invention will be presented in the following with reference to the drawings which serve merely the purpose of illustration and are not to be interpreted in a limiting way. Features of the invention disclosed by the drawings should be viewed as belonging to the invention individually and in any combination. In the drawings.

DETAILED DESCRIPTION OF VARIOUS EMBODIMENTS

Various embodiments of the present invention will now be described more fully hereinafter with reference to the accompanying drawings, in which some, but not all embodiments of the invention are shown. Indeed, embodiments of the invention may be embodied in many different forms and should not be construed as limited to the embodiments set forth herein. Rather, these embodiments are provided so that this disclosure will satisfy applicable legal requirements. Unless otherwise defined, all technical and scientific terms used herein have the same meaning as commonly known and understood by one of ordinary skill in the art to which the invention relates. The term "or" is used herein in both the alternative and conjunctive sense, unless otherwise indicated. Like numbers refer to like elements throughout.

Understood by a distal direction in the following is any direction in which an end of a measuring device points that is being inserted into a body tissue. This end is thus the distal end.

Figure 1:
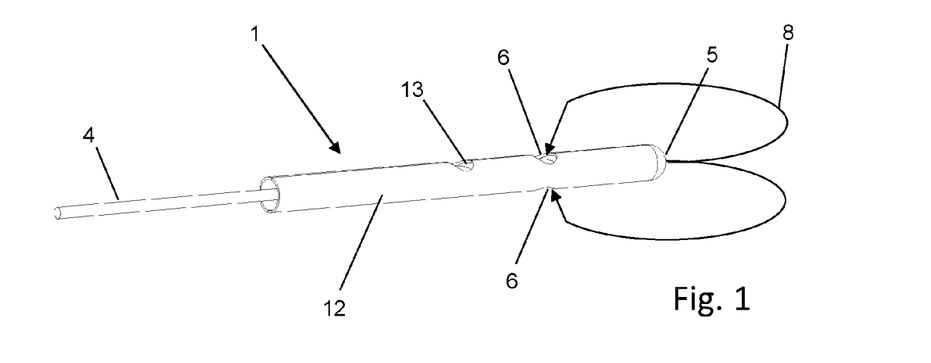
FIG. 1 shows a three-dimensional representation of a measuring probe according to the present invention.
Figure 2:
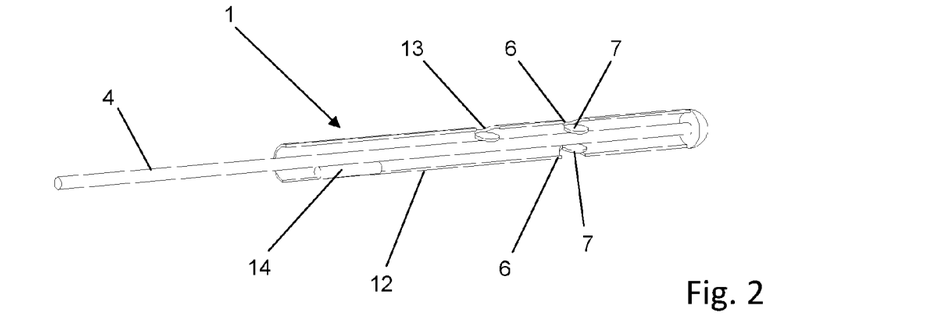
FIG. 2 shows a longitudinal section through a measuring device according to FIG. 1.

Shown in FIGS. 1 and 2 is a measuring device for measuring parameters of a body tissue using an elongated probe 1 for insertion into the body tissue. The measuring device comprises at least one first optical guide 2 and a second optical guide or an electrical conductor 3, which are guided in a line 4 through a solid cylindrical housing 12 of the probe 1. The first optical guide 2 transmits light rays from a light source (not shown) at a distal end of the probe 1. The probe 1 has an exit region 5, out of which light rays of the first optical guide emitted out of the optical guide exit out of the probe into the body tissue. The probe 1 further comprises two oppositely situated receiving regions 6, through which light rays reflected and/or scattered in the body tissue enter into the probe as input light rays. The input light rays are transmitted by the second optical guide or an electrical conductor 3. Provided for example is a processing device (not shown), for instance in the form of a computer, which directs the emission of light rays and receives the input light rays as measuring signal and processes these in such a way that parameters of the body tissue are determined therefrom. The measuring probe further comprises a pressure sensor 13 and a temperature sensor 14.

The exit region 5 at the distal end of the probe 1 is oriented in longitudinal direction of the probe, i.e. a surface normal or a symmetry axis of the exit region 5 points in direction of the longitudinal axis. Emitted light rays thus exit at least partially in longitudinal direction of the probe out of this probe. The oppositely situated receiving regions 6 are provided on a lateral circumferential region of the probe 1, and are disposed spaced apart from the exit region 5. The receiving regions 6 have e.g. a photocell 7, with which the input light rays are able to be captured. The receiving regions 6, or respectively the photocells in the embodiment shown, are oriented in radial direction to the longitudinal axis of the probe, i.e. their surface normal is perpendicular to the longitudinal axis of the probe. The spacing between the exit region 5 and the receiving regions 6 amounts to 5 mm, for example.

As can be seen in FIG. 1, a bundle 8 of emitted light rays exits for the most part substantially in longitudinal direction of the probe 1, and enters into the body tissue situated in distal direction in front of the probe 1. The light rays are scattered, reflected and/or absorbed on the body tissue, and are thus diverted from their New direction, and are changed in their intensity. A part of the diverted light rays enters the probe 1 again at the receiving regions 6, and is transmitted to the processing device as measurement signal. Since the emitted light rays are radiated at least partially in distal direction, they must undergo at least a deflection of 90° in order to be able to reach one of the receiving regions 6.

Figure 3:
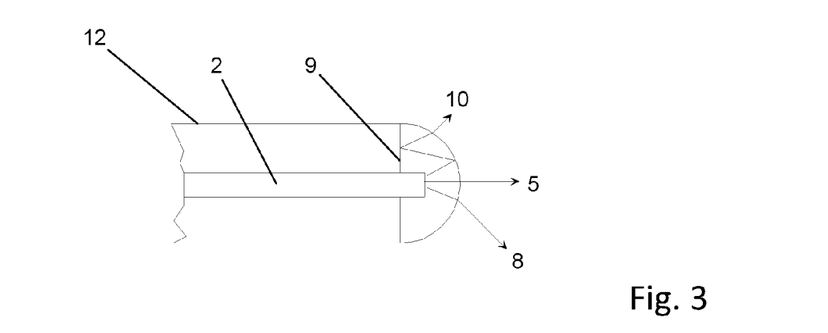
FIG. 3 shows a detailed view of a distal end of a measuring device with an optical element.

Shown in FIG. 3 is another embodiment of the measuring device according to the present invention in which provided at the distal end of the probe 1 is a reflection surface 9 and an optical element 10 disposed above. The reflection surface 9 closes off in distal direction an inner cavity 11 of the probe 1, the first optical guide 2 being guided a little bit through an aperture of the reflection surface 9 and ending in front of the optical element 10. The reflection surface 9 has at least on the distal side a reflecting surface which is suitable for reflecting the light rays generated by the light source. The emitted light rays are radiated by the material of the optical element, and are diffracted away from the longitudinal axis of the probe at least during exit from the surface of the optical element 10. For this purpose the optical element 10 provided is made of a material that is optically denser than the adjacent material of the body tissue, and it has an outwardly convex surface that runs symmetrically around the longitudinal axis. The optical element 10 thus deflects the emitted light rays before they exit out of the exit region of the probe. If part of the rays are reflected back at the surface of the optical element, these rays can be reflected on the reflection surface 9, and thus be sent back again into the body tissue.

A measuring device for measuring parameters of a body tissue according to the present invention thus has an elongated probe for insertion into the body tissue. The probe can have e.g. a cylindrical or also a flattened shape. The probe has a stiff section at the distal end, such as for example a stiff cover or a stiff housing, with which it can be inserted into the body tissue. Such a section is already to be understood as stiff when there is sufficient stability to be able to insert the probe into the body tissue. As a rule, such a section is stiffer than an adjacent element of the probe, such as a catheter tube or the like, for instance, but can however have a certain flexibility or yieldingness in order to make possible a gentle insertion. The stiff section can be provided at one end of a flexible line, such as a catheter tube, for instance. At least one optical or electrical line is provided for transmission of light rays, which line runs substantially along the longitudinal axis of the probe inside the probe, and is guided to the probe through the flexible line. The probe comprises an exit region, out of which exit light rays emitted from the optical guide exit out of the probe into the body tissue, after which the light rays are reflected, scattered and/or absorbed on the body tissue. The probe further comprises a receiving region through which input light rays reflected and/or scattered in the body tissue enter the probe e.g. on a photo detector and/or in an optical guide. For the case of the optical guide, separate optical guides are provided inside the probe for an emitted light ray and a reflected or respectively scattered input light ray. It is not excluded, however, that one optical guide is able to transmit a light ray that exits the probe for measuring the parameters and also a light ray that has been reflected or scattered in the body tissue. The at least one optical guide, or in the case of the photo detector at least one electrical transmission medium can transmit the input light rays as measurement signal to a processing device which determines the parameters to be measured using the input light rays. This can take place e.g. in a known way through analysis of the light intensity or the wavelengths of the input rays in comparison with the emitted light rays. The processing device can be used also for directing the emitted light rays.

According to the present invention, the exit region is provided on the distal end of the probe, and is oriented at least partially in longitudinal direction of the probe. It is thus oriented in beam direction of the light rays guided in the optical guide. The exit region can be situated on a front side of the probe. The exit region can be designed to be approximately symmetrical around the longitudinal axis, and can form the distal termination of the probe. Preferably the surface normal of the exit region coincides with the longitudinal axis of the probe. The light rays emitted out of the exit region exit in distal direction at least partially in longitudinal direction of the probe out of this probe. Preferably the direction of the ray exit out of the exit region lies on the longitudinal axis of the probe. Hence the direction of propagation of the emitted light rays has at least one vector portion which is directed parallel to the longitudinal axis of the probe, respectively of the emitting optical guide, in the direction of the body tissue lying in front of the probe. The emitted light rays can form a bundle of light rays which exit out of the exit region, for example in a straight line along the longitudinal axis, or are also emitted in a cone-shaped way symmetrically around the longitudinal axis, e.g. at an angle to the longitudinal axis.

The at least one receiving region is provided on a lateral circumferential region of the probe in a way spaced apart from the distal end of the probe and thus also spaced apart from the exit region. Thus the receiving region is formed substantially in radial direction to the longitudinal axis. The receiving region can be provided e.g. by means of an aperture or a transparent window in the jacket of the probe. The receiving region serves the purpose of capturing light scattered or reflected on the body tissue. For this purpose the input rays strike a photo detector, for instance, which is provided at the receiving region and is connected to an electrical conductor, or are fed to an optical guide by means of an optical element that is disposed in the probe. A multiplicity of receiving regions can be provided in a distributed way encircling the probe or in longitudinal direction of the probe. An own electrical or optical guide can be provided for each receiving region, or a joint optical guide is used. Received with the receiving region can be preferably both input light rays that run substantially radially to the probe axis, i.e. perpendicular to the receiving region, and also run approximately parallel to the probe axis as well as all input rays running at an angle between these directions.

According to the method for measuring parameters of a body tissue using an above-described measuring device, emitted light rays exit the probe or respectively exit out of the light guide at least partially in longitudinal direction at the distal end of the probe out of the probe, and enter again at a lateral circumferential region of the probe in a way spaced from this exit region, these input light rays entering at a receiving region being subjected to a deflection of more than 90° relative to light rays emitted out of the exit region. Since the direction of propagation of the emitted light rays has at least one small vector portion which is directed from the probe distally forward, i.e. away from at least one receiving region, they must be deflected by more than 90° in order to reach a receiving region and be received as measuring signal. The majority of the emitted light rays are emitted as a rule along the longitudinal axis of the probe, so that predominantly a deflection by more than 190° is necessary so that the input light rays are able to strike the receiving region. It is thus ensured that the emitted light rays undergo a deflection through reflection or scattering at the body tissue before they arrive at the receiving region as input light rays. Excluded can be an exit out of the probe and immediate entrance into the probe without an interaction with the body tissue taking place, as can happen with conventional measuring probes, for example, the receiving area and the exit area being identical or the emitted light rays running along the probe approximately within a guide channel for the probe without entering the body tissue. The light rays are not able to take any bypass course.

As a rule the majority of the emitted rays exit out of the probe at least approximately along the longitudinal axis of the probe, or respectively of the optical guide, and enter the probe again at the receiving region preferably approximately radially to the longitudinal axis of the probe. Thus most of the emitted light rays undergo a deflection in a range of about 270° until entering at a receiving region.

Thus with a measuring device according to the present invention the exit region and the entrance region can lie close to one another and the probe can be constructed shorter without the measuring signal being disadvantageously influenced thereby. The body tissue is thereby less stressed during insertion of the measuring device. Through a symmetrical arrangement of the exit region and the entrance regions around the longitudinal axis of the probe the region of the tissue that will be measured can be determined in a simple way through localization of the position of the probe. It is not necessary to capture an alignment of the probe at a particular position. With the method according to the invention, parameters can be captured relating to blood flow, hemoglobin values, water stored in the brain tissue or diverse markers.

Provided the alignment of the probe is known and individual electrical or optical guides for various receiving regions are used, the evaluation of the parameters can take place for certain subregions around the probe which are assigned to a receiving region. The evaluation of the parameters can thereby be refined.

In one embodiment of the measuring device a spacing of between 1 and 40 mm, preferably between 3 and 20 mm, is provided between an exit region and a receiving region. Preferably a multiplicity of receiving regions are provided in a way distributed around the circumference of the probe with the same spacing to the exit region. Provided can be, for instance, two diametrally opposed receiving regions or three, four or more preferably symmetrically disposed receiving regions distributed around the circumference. The firm section of the probe, e.g. in the form of a stiff cover or a firm housing, has in one embodiment maximally a length of 50 mm. It preferably has a length of about 20 mm and very preferably 12 mm.

In a variant, the exit region can be provided e.g. as exit aperture or exit window in the probe housing or in a probe cover, through which the light rays emitted out of the light guide exit out of the probe.

In another variant of the measuring device, the exit region can comprise an optical element which terminates the distal end of the probe. The optical element can have a convex or conically outwardly directed surface, the radial diameters tapering in distal direction. Light rays emitted out of the optical guide thus run through the optical element before they exit out of the probe. The optical element itself can form the exit region. The optical element can consist of the same material as the cover around the probe or as the probe housing. For example, the optical element can be made of epoxy resin or a material having comparable optical features such as e.g. polycarbonate, glass, acrylate, polypropylene, polyimide. It is advantageous if the optical element is made of a material with a higher refraction index than the adjacent tissue or the adjacent material. Thus emerging from the optical guide are exiting light rays which run through the optical element on the surface of the optical element in such a way that they are diffracted away from the longitudinal axis of the probe. Also conceivable in principle is the use of a grating which is put into a material that is disposed over the optical guide. Preferably the emitted light ray is widened into a cone of light on the optical element at the distal end of the probe, which cone of light covers a larger region of the body tissue than a light ray exiting directly out of the optical guide. The optical element thus diverts the light rays emitted out of the optical guide in the direction of the at least one receiving region in such a way that a vector portion of the direction of propagation remains in distal direction. The optical element is preferably designed symmetrical around the longitudinal axis of the probe, and forms the distal termination of the probe, which penetrates into the body tissue. The furthermost situated distal region of the optical element is preferably of blunt or respectively curved design, e.g. spherical or elliptical. The optical element can be made of solid material. It can seal off the exit opening of the emitting optical guide. In principle the optical element can have a coating on its surface, for example, which makes easier the insertion of the probe into the body tissue or which supports the diffraction of the light rays.

Furthermore, at the distal end of the probe, the measuring device can have a reflection surface with an aperture through which the optical guide emerges. The emitted light rays are then guided through the aperture and are emitted in distal direction behind the reflection surface. The reflection surface can close off e.g. a cavity of the probe which receives the at least one optical guide. One end of the optical guide emitting the light rays can protrude a little bit through the reflection surface or terminate in a way flush therewith. The reflection surface is preferably aligned perpendicular to the longitudinal axis of the probe, or respectively to the radiation direction of the optical guide. The reflection surface serves the purpose of reflecting back in the direction of the body tissue light rays that are reflected or scattered in the direction of the exit region.

The optical element on the distal end of the probe can be directly adjacent to the reflection surface. It is also possible to dispose the reflection surface on the optical element itself. The optical element can be disposed behind the reflection surface in distal direction. The exit of the emitted light rays out of the optical guide thus lies at or behind the reflection surface and in front of the surface of the optical element. Thus light rays that are possibly reflected on the surface of the optical element can be reflected back to the surface from the reflection surface, so that these light rays do not become lost for the examination of the body tissue.

Light rays with different wavelengths can be used for measuring the parameters in the body tissue. Preferably used is light in the infrared range with one or more wavelengths in the range of between 600 nm and 1000 nm. Light rays with different predetermined wavelengths can also be used that are sent into the body tissue at staggered intervals and in a pulsed way.

In principle further sensors can also be provided on the probe, such as, for example, sensors for temperature or pressure measurement.

A measuring device and a method according to the present invention are particularly suitable for measuring cerebral tissue in that the probe is inserted into the tissue approximately perpendicular to the cranium surface. Since the emission of the light rays takes place at least partially in distal direction, i.e. in direction of insertion of the probe into the tissue, the probe needs to be put less far into the tissue than in the case of a radial emission, in order to be able to measure the same tissue region. Damage to the tissue from the insertion of the probe is thereby minimized.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

LIST OF REFERENCE NUMERALS 1 probe
2 first optical guide
3 second optical guide
4 line
5 exit region
6 receiving region
7 photocell
8 bundle of rays
9 reflection surface
10 optical element
11 cavity
12 housing
13 pressure sensor
14 temperature sensor

The invention claimed is:

1. A measuring device for measuring parameters of a body tissue using an elongated probe (1) for insertion into the body tissue, comprising:
   at least one optical guide (2) for transmitting light rays, wherein the at least one optical guide (2) runs along the longitudinal axis of the probe within the probe from a distal end to an opposing proximal end of the probe;
   an exit region (5), from which light rays emitted from the optical guide exit into the body tissue and out of the probe;
   a plurality of receiving regions (6), through which light rays, which are at least one of reflected or scattered in the body tissue and that have exited from the exit region (5), enter the probe as input light rays on a photo detector or in an optical guide (2; 3); and
   a reflection surface (9) oriented in a direction that is transverse to the longitudinal axis of the probe, the reflection surface (9) comprising an opening through which the at least one optical guide (2) extends, the light rays emitted being guided through the opening and travelling in a distal direction that extends from the proximal end toward the distal end of the probe;
   wherein:
      the exit region (5) is positioned at the distal end of the probe (1) and is oriented in the longitudinal direction of the probe (1), so that light rays emitted by the probe (1) exit the probe (1) such that the light rays emitted travel in a straight line along the longitudinal direction of the probe (1); and
      the plurality of receiving regions (6) is spaced at a longitudinal distance toward the proximal end of the probe (1) and away from the exit region (5), the at least one receiving region (6) being positioned on a lateral circumferential region of the probe (1).

2. The measuring device according to claim 1, wherein the plurality of receiving regions (6) is oriented substantially radially with respect to the longitudinal axis of the probe (1).

3. The measuring device according to claim 1, wherein the plurality of receiving regions (6) are provided distributed around the probe (1) in a circumferential direction.

4. The measuring device according to claim 1, wherein the bundle (8) of light rays emitted are focused substantially in such a way that these light rays exit out of the optical guide (2) symmetrically around the longitudinal axis of the probe (1).

5. The measuring device according to claim 1, wherein the spaced distance between the exit region (5) and the receiving region (6) measures between 1 and 40 mm.

6. The measuring device according to claim 1, wherein the probe (1) has a rigid section (12) having maximally a length of 50 mm.

7. The measuring device according to claim 1, wherein the exit region (5) comprises an optical element (10) which terminates at the distal end of the probe (1).

8. The measuring device according to claim 7, wherein the optical element (10) is made of a material having a greater refraction index than an adjacent material of the body tissue.

9. The measuring device according to claim 7, wherein the optical element (10) is made of at least one of: an epoxy resin, a polycarbonate material, a glass material, an acrylate material, a polypropylene material, or a polyimide material.

10. The measuring device according to claim 1, wherein the optical element (10) is disposed in distal direction behind the reflection surface (9).

11. The measuring device according to claim 1, wherein the emitted light rays have one or more wavelengths in the range between 600 nm and 1000 nm.

12. A method for measuring the parameters of a body tissue using a measuring device according to claim 1, input light rays entering at a receiving region (6) being subjected to a deflection of more than 90° relative to light rays emitted from the exit region (5).

13. The method according to claim 12, wherein a predominant portion of the emitted light rays are subjected to a deflection in the range of about 270° until entrance at a receiving region (6).

14. The method according to claim 12, wherein light rays exiting out of the optical guide (2) are diffracted away from the longitudinal axis of the probe (1), on a surface of the optical element (10).

15. The method according to claim 1, wherein the at least one optical guide (2) runs along the longitudinal axis of the probe and within the probe, such that the light rays transmitted there-through and emitted there-from travel along the longitudinal axis.

16. The method according to claim 1, wherein the light rays re-enter the probe after having been at least one of reflected or scattered in and exited from the body tissue.

* * * * *

UNITED STATES PATENT AND TRADEMARK OFFICE
CERTIFICATE OF CORRECTION

PATENT NO. : 9,668,681 B2
APPLICATION NO. : 14/115456
DATED : June 6, 2017
INVENTOR(S) : Frohlich et al.

It is certified that error appears in the above-identified patent and that said Letters Patent is hereby corrected as shown below:

Delete drawing sheet 1/1, and substitute therefor the drawing sheet consisting of FIGs 1-3, as shown on the attached page.

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*